United States Patent [19]

Hrib et al.

[11] Patent Number: 5,045,546
[45] Date of Patent: Sep. 3, 1991

[54] 8-AZABICYCLO[3.2.1]OCTYLALKYL-THIAZOLIDINES

[75] Inventors: Nicholas J. Hrib, Somerville; John G. Jurcak, Somerset, both of N.J.

[73] Assignee: Hoechst-Roussel Pharmaceuticals Inc., Somerville, N.J.

[21] Appl. No.: 603,491

[22] Filed: Oct. 26, 1990

[51] Int. Cl.$^5$ .................. A61K 31/44; C07D 417/06
[52] U.S. Cl. ....................................... 514/304; 546/125
[58] Field of Search ........................ 514/304; 546/125

[56] References Cited

U.S. PATENT DOCUMENTS

| | | | |
|---|---|---|---|
| 2,804,460 | 8/1957 | Cavallito | 546/125 |
| 4,261,990 | 4/1981 | Bowman | 546/125 |
| 4,933,453 | 6/1990 | Hrib | 544/297 |

Primary Examiner—Catherine S. Kilby Scalzo
Attorney, Agent, or Firm—Raymond R. Wittekind

[57] ABSTRACT

Novel 8-azabicyclo[3.2.1]octylalkylthiazolidinones of the formula

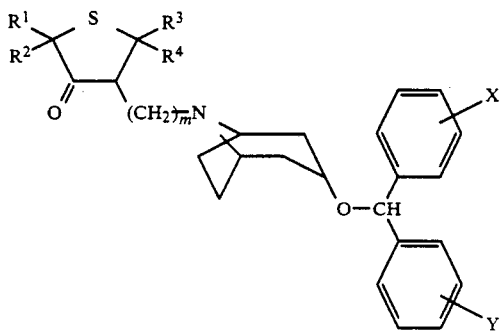

where $R^1$, $R^2$, $R^3$, $R^4$, m, x and y are defined herein, process for the preparation thereof, and methods of treating psychoses and alleviating pain employing compounds and compositions thereof are disclosed.

6 Claims, No Drawings

8-AZABICYCLO[3.2.1]OCTYLALKYLTHIAZOLIDINES

DESCRIPTION OF THE INVENTION

The present invention relates to 8-azabicyclo[3.2.1]octylalkylthiazolidinones. More particularly, the present invention relates to 3-diphenylmethoxy-8-azabicyclo[3.2.1]octylalkylthiazolidinones of formula 1

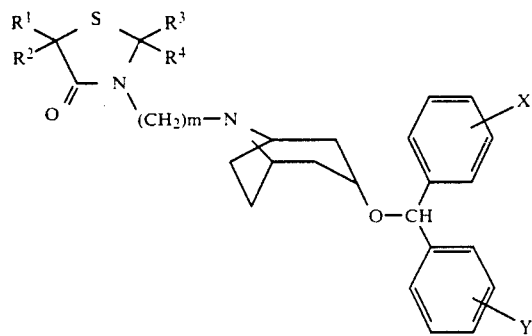

wherein $R^1$ and $R^2$ are independently hydrogen or alkyl; $R^3$ and $R^4$ are independently hydrogen or alkyl; X and Y are independently hydrogen, alkyl, alkoxy, halogen or trifluoromethyl; m is 2,3, or 4, or an optical isomer thereof; or a pharmaceutically acceptable acid addition salt thereof, which are useful for treating psychoses, alone or in combination with inert adjuvants.

Preferred 3-diphenylmethoxy-8-azabicyclo[3.2.1]octylalkylthiazolidinones are those wherein $R^1$ and $R^2$ are independently hydrogen or alkyl and m is 4.

As used through the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy and the like; the term "halogen" refers to a member of the family consisting of chlorine, fluorine, bromine or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof. The formulas of the compounds shown herein are intended to encompass all possible optical isomers of the compounds so depicted.

The novel 8-azabicyclo[3.2.1]octylalkylthiazolidinones of formula 1, the compounds of the present invention, are prepared by condensing a 3-(haloalkyl)-4-thiazolidinone of formula 2

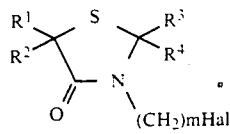

wherein $R^1$, $R^2$, $R^3$, $R^4$, and m are as hereinbeforedescribed and Hal is halogen, the preparation of which is described in U.S. patent application Ser. No. 430,688 filed Oct. 31, 1989, now U.S. Pat. No. 4,933,453 issued June 12, 1990, with a 3-diphenylmethoxy-8-azabicyclo[3.2.1]octane of formula 3

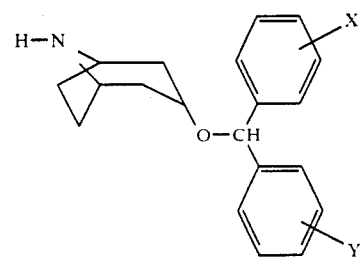

wherein X and Y are as hereinbefore described. The condensation is conveniently performed by treating the halide 2 with the azabicyclo[3.2.1]octane 3 in the presence of an acid acceptor, a displacement promoter and a suitable solvent. Among acid acceptors, there may be mentioned alkali metal carbonates and alkali metal bicarbonates such as, for example, lithium carbonate, sodium carbonate and potassium carbonate, and lithium bicarbonate, sodium bicarbonate and potassium bicarbonate. Potassium carbonate is preferred. Among displacement promoters, there may be mentioned alkali metal halides such as, for example, sodium iodide and potassium iodide, and sodium bromide and potassium bromide. Potassium iodide is preferred. Among suitable solvents, there may be mentioned, for example, dimethylformamide, dimethylacetamide, dimethylsulfoxide, hexamethylphosphoramide, and acetonitrile. Acetonitrile is preferred. The temperature at which the condensation is conducted is not narrowly critical. It is desirable, however, to perform the condensation at a temperature within the range of about 50° C. to about the reflux temperature of the condensation medium to assure a reasonable rate of conversion. A reaction temperature within the range of about 70° C. to about the reflux temperature of the condensation medium is preferred.

The 8-azabicyclo[3.2.1]octylalkylthiazolidnones of the present invention are useful for treating psychoses by virtue of their ability to block apomorphine-induced climbing in mammals.

Antipsychotic activity is determined in the climbing mice assay by a method similar to those described by P. Protais et al., Psychopharmacol., 50,1 (1976) and B. Costall, Eur. J. Pharmacol., 50, 39 (1978).

The subject CK-1 male mice (23–27 grams) are group-housed under standard laboratory conditions. The mice are individually placed in wire mesh stick cages (4"×4"×10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |
| 4 paws on the wall (full climb) | 2 |

Mice consistently climbing before the injection of apomorphine will be discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score; 6 per mouse over 3 readings) and the total score of the control group (vehicle intraperitioneally-apomorphine subcutaneously) is set to 100%. $ED_{50}$ values with 95% confidence limits are calculated by a Linear Regression Analysis. Antipsychotic activity expressed as the $ED_{50}$ value of representative 8-azabicyclo[3.2.1]octylalkylthiazolidinones as well as two standard antipsychotics are presented in Table I.

TABLE I

| Compound | Antipsychotic Activity $ED_{50}$ (mg/kg) |
|---|---|
| 3-[4-[3-(diphenylmethoxy)-8-azabicyclo[3.2.1]octan-8-yl]-butyl]-5-methyl-4-thiazolidinone hydrochloride | 12.1 |
| 3-[4-[3-(diphenylmethoxy)-8-azabicyclo[3.2.1]octan-8-yl]-butyl]-5,5-dimethyl-4-thiazolidinone hydrochloride | 7.73 |
| haloperidol (standard) | 0.16 |
| thioridazine (standard) | 4.1 |

Antipsychotic activity is achieved when the present 8-azabicyclo[3.2.1]octylalkythiazolidinones are administered to a subject requiring such treatment as effective oral, parenteral or intravenous dose of from 0.01 to 50 mg/kg of body weight per day. A particularly preferred effective range is about 1 to 5 mg/kg of body weight per day. It is to be understood, however, that for any particular subject, specific dosage regimens should be adjusted to the individual need and the professional judgement of the person administering or supervising the administration of the aforesaid compound. It is to be further understood that the dosages set forth herein are exemplary only and they do not, to any extent, limit the scope or practice of the invention.

Potential for undersirable extrapyramidal side effect activity is determined in the inhibition of apomorphine stereotypy assay by a method similar to those described by N. E. Anden, et al., J. Pharma. Pharmacol., 19, 627, (1967), and A. M. Ernst, et al., Psychopharmacologia (Berl.), 10, 316 (1967).

In this assay, groups of male Wistar rats (125–200 grams) are used and food and water are available ad libitum. Drugs are prepared using distilled water and, if insoluble, a suitable surfactant is added. The route of administration may be varied and the dosage volume is 10 ml/kg. For a primary screen, a group size of six is used. Drug is administered one hour prior to scoring and the animals are placed in individual clear plastic cages (24×14×13 cm). The control group receives vehicle. Apomorphine hydrochloride solution is prepared at a concentration of 15 mg/10 ml in a 0.03% ascorbic acid stock solution (30 mg of ascorbic acid in 100 ml of 1% saline) to increase the stability of the apomorphine hydrochloride while in solution. Apomorphine hydrochloride solution is administered at a dose of 1.5 mg/kg subcutaneous (s.c.) with a dosage volume of 1 ml/kg. Fifty minutes after drug dosing, stereotypic behavior is noted. Stereotypic activity is defined as sniffing, licking or chewing behavior that occurs in a repetitive manner and is rated as follows: Constant sniffing, licking or chewing without interruption; the animal is considered protected if this behavior is interrupted.

The percent effectiveness of a drug is determined by the number of animals protected in each group. Antipsychotics displaying little effect in this assay would be expected to show a low propensity to cause undersirable extrapyramidal side effects and/or tardive dyskinesias in mammals (N. C. Moore and S. Gershon, Clinical Neuropharmacology, 12, 167, (1989).

A dose-response is run in the same manner as a primary screen except that a group size of 10 is used and the animals are dosed in a randomized manner. One group receives vehicle. $ED_{50}$ for stereotypy are calculated by means of probit analysis.

Inhibition of apomorphine induced stereotypy of respresentative 8-azabicyclo[3.2.1]octylalkylthiazolidinones of the present invention and two standards is given in Table II.

TABLE II

| Compounds | Dose (mg/kg body wt.) | % Inhibiton of apomorphine induced stereotypy |
|---|---|---|
| 3-[4-(3-diphenylmethoxy)-8-azabicyclo[3.2.1]octan-8-yl]-butyl]-5-methyl-4-thiazolidinone hydrochloride | 20 | 0 |
| 3-[4-(3-diphenylmethoxy)-8-azabicyclo[3.2.1]octan-8-yl]-butyl]-5,5-dimethyl-4-thiazolidinone hydrochloride | 40 | 17 |
| haloperidol | 0.2 | 50 |
| thioridazine | 16 | 50 |

Compounds of the invention include:
a. 3-[2-[3-(diphenylmethoxy)-8-azabicyclo[3.2.1]octan-8-yl]ethyl]-5,5-dimethyl-4-thiazolidinone;
b. 3-[3-[3-(diphenylmethôxy)-8-azabicyclo[3.2.1]octan-8-yl]propyl]-5,5-dimethyl-4-thiazolidinone;
c. 3-[4-[3-(2-methylphenylphenylmethoxy)-8-azabicyclo[3.2.1]octan-8-yl]butyl]-5,5-dimethyl-4-thiazolidinone;
d. 3-[4-[3-(2-bromophenylphenylmethoxy)-8-azabicyclo[3.2.1]octan-8-yl]butyl]-5,5-dimethyl-4-thiazolidinone; and
e. 3-[4-[3-(2-trifluorophenylmethoxy)-8-azabicyclo[3.2.1]octan-8-yl]butyl]-5,5-dimethyl-4-thiazolidinone.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobsic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

3-[4-(3-Diphenylmethoxy)-8-azabicyclo[3.2.1]octan-8-yl]butyl]-5-methyl-4-thiazolidinone hydrochloride A mixture of 3-(4-bromobutyl)-5-methyl-4-thiazolidinone (4.5 g), 3-(diphenylmethoxy)-8-azabicyclo[3.2.1]octane (5.25 g), potassium carbonate (5.0 g), and sodium iodide (200 mg) in dry acetonitrile (160 ml) was heated for 6 hrs under reflux, under nitrogen, with stirring. The reaction mixture was allowed to cool to room temperature and was stirred for an additional 48 hrs. The mixture was then filtered, and the filtrate was concentrated in vacuo. The residue was chromatographed on silica using 1:1 methanol:dichloromethane as the eluant. Appropriate fractions were collected, combined, and concentrated in vacuo. The residue was taken up in diethyl ether, and the hydrochloride was precipitated by the addition of hydrogen chloride in diethyl ether. The precipitate was collected and recrystallized from dichloromethane:diethyl ether to provide 4.17 g (46.4%) of product, mp 200°–203° C.

ANALYSIS Calculated for $C_{28}H_{37}ClN_2O_2S$: 67.11% C; 7.44% H; 5.59% N. Found: 67.15% C; 7.43% H; 5.58% N.

EXAMPLE 2

3-[4-(3-Diphenylmethoxy)-8-azabicyclo[3.2.1]octan-8-yl]butyl-5,5-dimethyl-4-thiazolidinone hydrochloride A mixture of 3-(4-bromobutyl)-5,5-dimethyl-4-thiazolidinone (5.00 g), 3-diphenylmethoxy-8-azabicyclo[3.2.1]octane (6.06 g), potassium carbonate (8.00 g), sodium iodide (250 mg), and acetonitrile (200 ml) was heated at 80° C. under nitrogen. After 18 hrs, the mixture was cooled to ambient temperature and filtered. The filter cake was washed with dichloromethane, and the filtrate was concentrated under reduced pressure. The residue was taken up in ether (230 ml), washed with 5% sodium hydroxide solution (2×100 ml), water (150 ml), brine (150 ml), dried over anhydrous sodium sulfate, and the filtrate was concentrated. The residue was purified by chromatography on silica gel, using 1% ammonium hydroxide:9% methanol:90% dichloromethane as eluant. The appropriate fractions were collected and combined. The hydrochloride salt was precipitated by the addition of hydrogen chloride in ether. Recrystallization from dichloromethane/ether afforded 2.20 g (22%) of product, mp 151°–153° C.

ANALYSIS: Calculated for $C_{29}H_{39}ClN_2O_2S$: 67.61% C; 7.63% H; 5.44% N. Found: 67.36% C; 7.53% H; 5.39% N.

We claim:

1. A compound of the formula

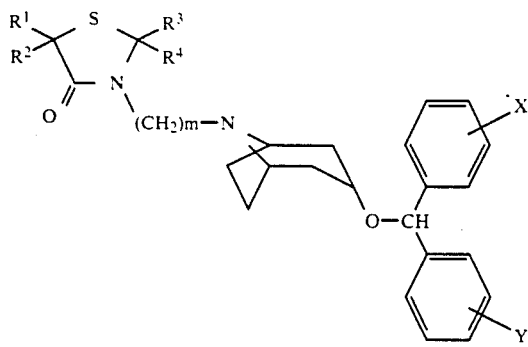

wherein $R^1$ and $R^2$ are independently hydrogen or loweralkyl; $R^3$ and $R^4$ are independently hydrogen or loweralkyl; X and Y are independently hydrogen, loweralkyl, loweralkoxy, halogen or trifluoromethyl; m is 2, 3, or 4; or an optical isomer thereof; or a pharmaceutically acceptable salt thereof.

2. A compound according to claim 1 wherein $R^1$ and $R^2$ are independently hydrogen or loweralkyl; and m is 4.

3. The compound of claim 2 which is 3-[4-(3-diphenylmethoxy)-8-azabicyclo[3.2.1]octan-8-yl]butyl-5-methyl-4-thiazolidinone.

4. The compound of claim 2 which is 3-[4-(3-diphenylmethoxy)-8-azabicyclo[3.2.1]octan-8-yl]butyl-5,5-dimethyl-4-thiazolidinone.

5. A method of treating psychoses comprising administering to a mammal in need of psychoses treatment a psychoses treating effective amount of a compound as defined in claim 1.

6. A psychoses treating composition comprising an inert psychoses treating adjuvant and, as the active ingredient, an amount effective in treating psychoses of a compound as defined in claim 1.

* * * * *